United States Patent
Kocher

(10) Patent No.: US 6,228,375 B1
(45) Date of Patent: May 8, 2001

(54) MICRO HAND SANITIZERS (MHS)

(76) Inventor: Robert William Kocher, 4828 3rd St. North, Arlington, VA (US) 22203

( * ) Notice: Subject to any disclaimer, the term of this patent is extended or adjusted under 35 U.S.C. 154(b) by 0 days.

(21) Appl. No.: 09/323,249

(22) Filed: Jun. 1, 1999

Related U.S. Application Data

(60) Provisional application No. 60/113,504, filed on Dec. 22, 1998.

(51) Int. Cl.[7] ........................................................ A61K 9/00
(52) U.S. Cl. ............................................ 424/400; 424/405
(58) Field of Search ................................... 424/451, 455, 424/400, 405

(56) References Cited

U.S. PATENT DOCUMENTS

| | | | | |
|---|---|---|---|---|
| 3,585,982 | * | 6/1971 | Hollinshead | 126/263 |
| 5,063,057 | * | 11/1991 | Spellman et al. | 424/401 |
| 5,089,269 | * | 2/1992 | Noda et al. | 424/456 |
| 5,380,534 | * | 1/1995 | Schurig et al. | 424/456 |

* cited by examiner

*Primary Examiner*—Thurman K. Page
*Assistant Examiner*—Liliana Di Nola-Baron

(57) ABSTRACT

This invention relates to a micro, single-use disposable packaging container with a volumetric capacity on the order of 0.25 to 2.0 milliliters, designed in various configurations which can durably be carried in a pocket containing a hand sanitizing solution or substance with an easy opening to allows the user to discreetly and frequently sanitize the hands from common bacteria, viruses or biological agents.

5 Claims, 5 Drawing Sheets

MICRO HAND SANITIZERS (MHS)

This appln claims the benefit of Provisional 60/113,504 filed Dec. 22.

BACKGROUND OF THE INVENTION

The present invention relates to a small, single-use, disposable container having various configurations which can durably be carried in a pocket and containing a hand-sanitizing solution or substance with easy opening capability to allow the user to discreetly and frequently sanitize the hands from common bacteria, viruses or biological agents.

BACKGROUND—PRIOR ART

Today's society involves increased secondary physical interactions with other people such as from door handles, table pens, sinks, towel dispensing machines, flushing handles, water fountains, shopping cart handles, on public transportation systems, public restrooms, and doors entering most buildings. Direct contact such as hand shaking can be particularly dangerous to transfer of germs since most people will rub their face or cover their mouth or nose when coughing or sneezing.

Current hand sanitizing methods in public location are typically washing of the hands in a rest room sink. This involves turning the water on-off by touching a potentially contaminated handle, turning a handle for a paper towel or pushing button for an air dryer—again touching a potentially contaminated surface, and finally grabbing on a door handle which has the most potential contamination when leaving the rest room. I have observed that approximately 50% of the men leaving a men's restroom do not wash their hands and contaminate the door handle. These individuals go on to greet others by shaking their hands potentially spreading contamination.

Paper or cloth towels in a small packet is another method for cleaning hands but this method involves a cumbersome process requiring two hands to tear open a packet, remove the towel, find someplace to through the packet away, unfold a towel, wipe both hands, through away the towel. The towel approach is more for cleaning hands covered with a foreign substance such as barbecue sauce, grease, butter, or other light substances.

Bottles of hand sanitizing lotions in bottles exist but are cumbersome to carry in a pocket and are intended for anywhere from 25 to 200 uses. These containers require a relatively large cap for opening and closing. Once opened there is the risk of a substantial quantity of leakage due to their high volume compared to a single use requirement. These bottles also require two hands to operate. Multi-use containers also require the passing from one person to another, again risking contamination on the outside of the bottle. Multi-use containers pose the challenge of dispensing the right quantity. Normally one must be very careful not to dispense too much. You must quickly focus on what you are doing and attempt to get the right amount out of the bottle.

U.S. Pat. No. 5,063,057 by Spellman, et all, entitled Cosmetic Capsules addresses the small packaging issues and requirements for cosmetic products. The MHS specific packaging configurations significantly differ in structure from the structure shown in U.S. Pat. No. 5,063,057. MHS's method use claim for hand sanitizing solutions is not addressed in Spellmen's patent.

Packaged towels and bottles are impracticable to use in social settings where an individual has shaken many hands and would like to discreetly sanitize his/her hand. Similarly, packaged towels are difficult to open in public areas such as subways or crowds of people and bottles are difficult to carry in shirt or pants pockets.

OBJECTIVES AND ADVANTAGES

The objective of the micro hand sanitizers (MHS) is to provided and more efficient method of carrying and using sanitizing solutions in public environments and in situation involving significant exposure to bacterial, viral and biological agents. MHS use can to help stop the spread of these bacterial, viral, and biological threats and protect the user from the most common way of contacting these threats. As used in this application, the term "sanitizing substance" includes compounds designed to defeat common household germs, bacterial, viruses and biological agents. Micro hand sanitizers (MHS) has significant advantages over current methods.

(a) The micro encapsulating container is significantly smaller than any other cleansing container with a substance volume of approximately 0.5 to 2.0 milliliters, just enough for a single use to sanitize both hands. This small size allows the MHS to be carried in a shirt, pants pocket, coat pocket, or larger quantities in a briefcase, or purse.

(b) The MHS's individual packaging allows the user to carry the quantity deemed necessary in a pocket and the remainder in the desk, briefcase or purse. The individual packaging also allows for a bowl or jar of MHS to be placed in restrooms, food preparation areas, or areas where bacterial, viral, or biological contamination may exist.

(c) The MHS is a single use system therefore the simple squeezing of a capsule squirts the right amount. MHS's single use size does not require the slow, careful watching of the quantity being dispensed. The user can focus on something else, such as watching a computer screen, watching the road while driving, involved in another activity.

(d) Several of MHS's easy to use single hand opening system allows one to discreetly sanitize one's hands in a group of people after shaking many hands and not bring about much attention.

DRAWING FIGURES

FIG. 1. shows a MHS capsule configuration with a notched tip serving as a closure for the encapsulating container.

FIG. 2. shows a partial view of a single notch in the tip.

FIG. 3. shows the capsule having applied pressure (arrows) and the ruptured notched tip.

FIG. 4. is a capsule configuration with a capped dispensing hole serving as a closure.

FIG. 5. shows a capsule configuration with a tape seal over a slit dispensing hole.

FIG. 6. shows a capsule configuration with two interlocking halves.

FIG. 7. shows a sphere configuration with a tape cover over a dispensing hole.

FIG. 8. shows a disk configuration with a tape cover over a dispensing hole.

FIG. 9. shows a disk configuration with a tape cover over a dispensing hole on the edge.

FIG. 10. shows a tube configuration with a tap cover over a dispensing slit.

FIG. 11. shows a tube configuration with pinched ends.

FIG. 12. shows a tube configuration with ends bent over.

FIG. 13. shows a flat pack configuration with tape covering a dispensing slit.

FIG. 14. shows a flat pack configuration with notched ends.

FIG. 15. shows a flat pack configuration with folded ends.

FIG. 16. Shows a flat pack configuration with jagged ends.

REFERENCED NUMERAL IN DRAWINGS

1. Capsule Configuration
2. Notch or Cut
3. Dispensing Hole Plug
4. Tape Covering Dispensing Hole
5. Tab to Pull or Lift-off Tape
6. Pre-cut Dispensing Hole or Slit
7. Outer Half of Two Piece Capsule
8. Inner Half of Two Piece Capsule
9. Sphere/Ball/"Egg" Configuration
10. Disk or Coin Configuration
11. Tube Configuration
12. Crimped End of Tube
13. Folded End of Tube
14. Flat Pack Configuration
15. Notched End of Flat Pack
16. Folded Ends of Flat Pack DESCRIPTION—FIGS. 1 to 3—Preferred Embodiment A preferred embodiment of the micro hand sanitizer (MHS) is a soft crushable material capsule with a volumetric capacity of approximately 0.25 to 2.0 milliliters of hand sanitizing solution. For example, a commonly used solution sold under the trademark "Purell" is one of the solutions which I contemplate using in my invention. Other custom formulas are envisioned. FIG. 1 depicts the general elongated capsule configuration. The capsule can be fitted with several different dispensing approaches. The first of these methods is shown in FIGS. 1–3. Item 2 depicts a small notch or semi-perforated hole made in the tip of the capsule during the manufacturing process. This hole or notch is cut deep enough such that when the sides of the capsule are squeezed hard between two fingers, the pre-cut area will rupture spraying the contents in the intended direction. The pre-cut end can be marked with an arrow or colored tip to make it easy for the user to identify out of which end the contents will spray.

Figure 4:
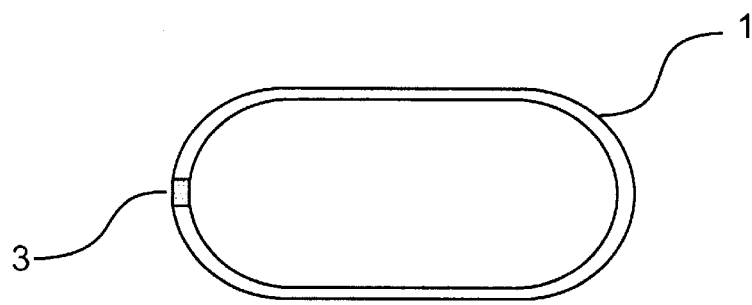
Figure 5:
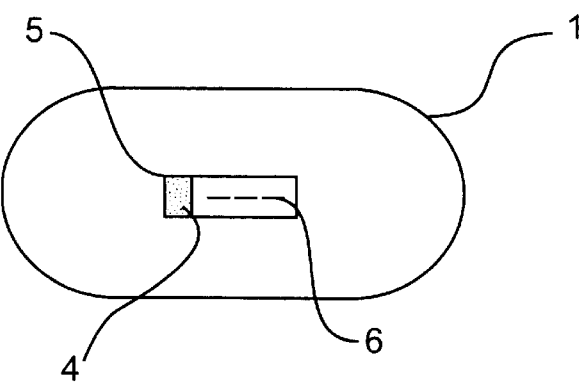
Figure 6:
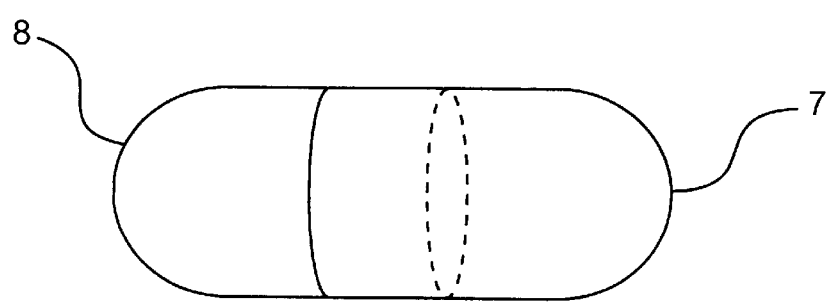

FIG. 4–6 Alternative Embodiments (Capsule)

FIG. 4 depicts a capsule configuration with pre-cut hole and cap configuration in the end of the capsule. Item 3 is a cap that is inserted in the pre-cut hole during the manufacturing process. This cap can be released either through pressure or can be scratched off with a fingernail. This dispensing configuration would allow single hand operation.

FIG. 5 depicts a capsule configuration with a pre-cut slit or hole, Item 6, covered with a tape, Item 4. During the manufacturing process, a small slit or hole is made in the capsule then covered with a tape or plastic cover. The tape, Item 4, can have a tab on the end to allow ease in prying up the end of the tape. A plastic cover could be pried up with a fingernail to allow one hand opening and dispensing of the solution.

FIG. 6 depicts a capsule configuration consisting of two halves, Item 7 and Item 8, whereby one half has a slightly smaller diameter and fits inside the other half. The dispensing mechanism is simply the separation of the two halves and pouring the solution into the hands.

Figure 7:
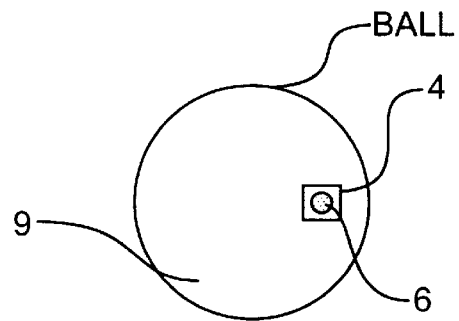

FIG. 7 Alternative Embodiments (Sphere)

FIG. 7 depicts a sphere, ball, or oblong egg configuration whereby a precut hole is made in the surface, Item 6, and covered with a tape or plastic. The tape or plastic can have a tab to allow ease in prying the cover off. Once the cover is off, the sphere is crushed and the solution is sprayed through the pre-cut hole. The notched or semi-perforated hole method could also be used.

Figure 8:
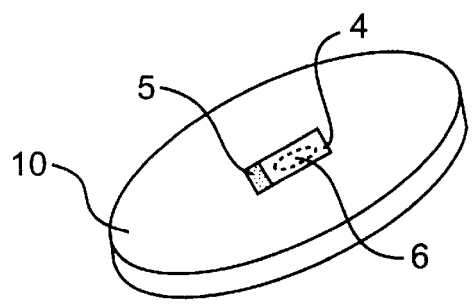
Figure 9:
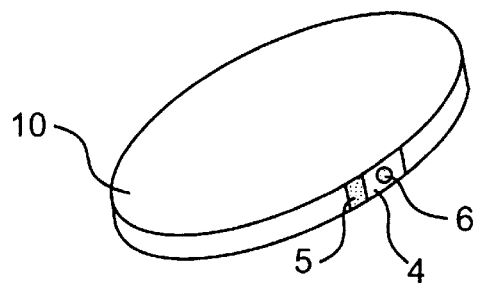

FIGS. 8–9 Alternative Embodiments (Disk)

FIG. 8 depicts a disk shaped enclosure, Item 10, with a pre-cut hole, Item 6, covered by a tape or plastic cover, Item 4, with an optional tab, Item 5. This disk configuration can resemble a coin to be carried along with pocket change.

FIG. 9 depicts a disk shaped enclosure with the closure and dispensing hole on the edge of the disk.

Figure 10:
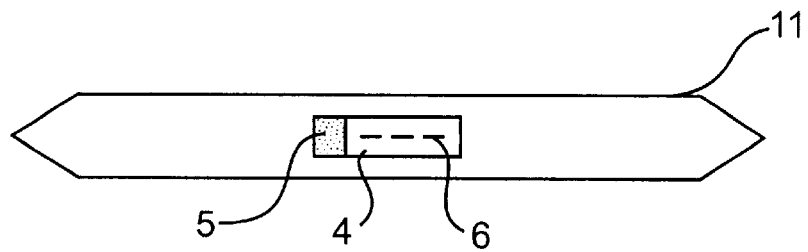
Figure 11:
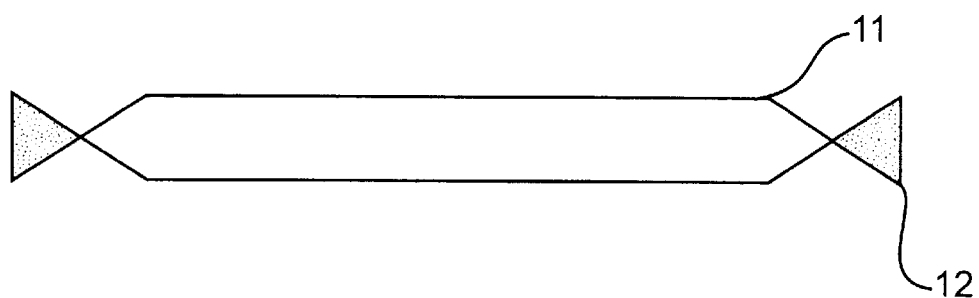
Figure 12:
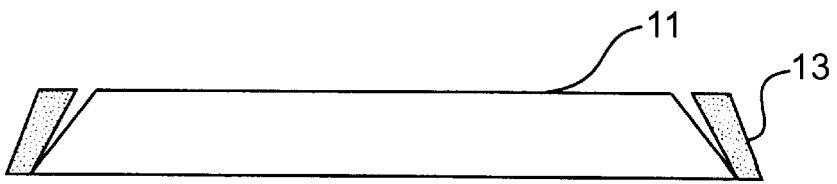

FIGS. 10–12 Alternative Embodiments (Tubes)

FIG. 10 depicts a tube shaped enclosure, Item 11. A tube shaped enclosure constructed from a small tube capable of holding less than 2.0 milliliters. FIG. 10 depicts the tube with sealed ends, a pre-cut slot, Item 6 covered by a tape or plastic, Item 4, with a tab, Item 6.

FIG. 11 depicts a tube shaped with sealed ends, Item 12, that are clamped closed to seal in the sanitizing solution. Once the clamp is removed the end becomes the dispensing opening.

FIG. 12 depicts a tube shaped enclosure, Item 11 with the ends folded back on itself Item 13, to seal in the sanitizing solution. The folded end can be held down by an adhesive. The folded end is opened by breaking the glue seal and folding back the end and squeezing the tube to dispense the solution though the end of the tube.

FIGS. 13–16 Alternative Embodiments (Flat Packs)

Figure 13:
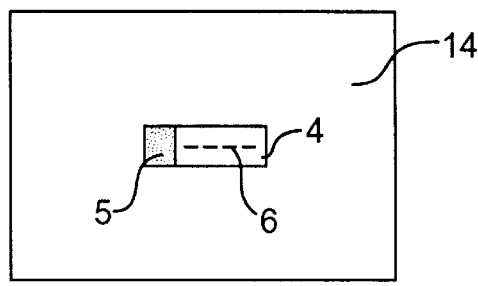

FIG. 13 depicts a flat pack shaped enclosure, Item 14. A flat pack is constructed from two sheets of material, usually flexible plastic sealed on the ends. FIG. 10 depicts a pre-cut slot, Item 6 covered by a tape or plastic, Item 4, with a tab, Item 6. Flat packs are very thin and fit easily in shirt pocket or pants pockets.

Figure 14:
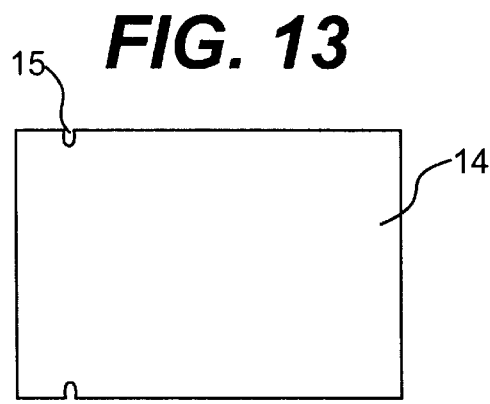

FIG. 14 depicts a flat pack shaped enclosure, Item 14, with one or two notches that can be torn off to dispense the solution.

Figure 15:
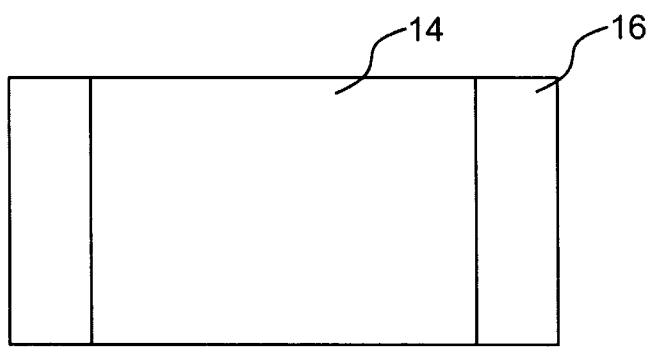

FIG. 15 depicts a flat pack shaped enclosure, Item 14, with the ends folded over on itself, Item 16, to seal in the solution. An adhesive can be used to hold the folded ends closed. The solution is dispensed by folding back the ends and squeezing the container.

Figure 16:
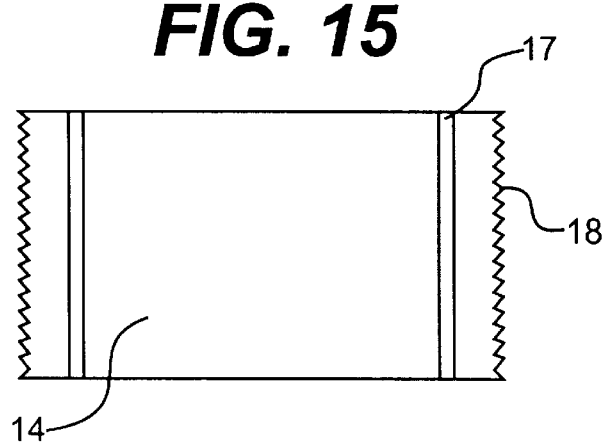

FIG. 16 depicts a flat pack shaped enclosure, Item 14, which is sealed along the edges, Item 17. Beyond the seals, the flat pack edges are cut in a jagged configuration. This jagged configuration allows the packed to be opened by tearing an end of the packet. The tearing is relatively easy since the jagged ends act as a line of numerous notches.

Advantages

From the description above, a number of advantages of the micro hand sanitizer (MHS) can be realized. The MHS allows for the practicable carrying of hand sanitizing solutions in single use quantities of about 0.25 to 2.0 milliliters in pockets where conventional bottles do not fit. Several of the MHS's dispensing system allows dispensing in a fraction of the time it takes conventional bottle, hand washing or towel systems. Several of the MHS's single hand opening techniques allow for inconspicuous use in crowded area. The simple addition of bleach to conventional solutions increases the bacterial, viral, and biological protection over current solutions.

Figure 1:
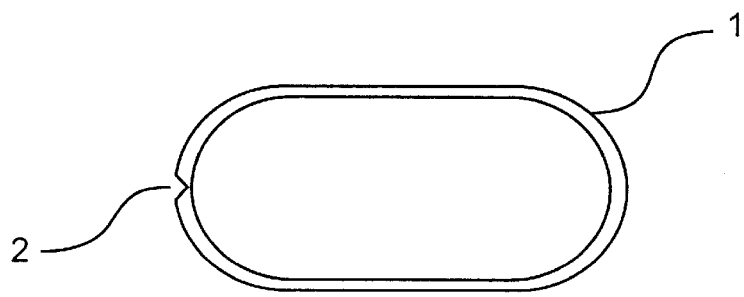
Figure 2:
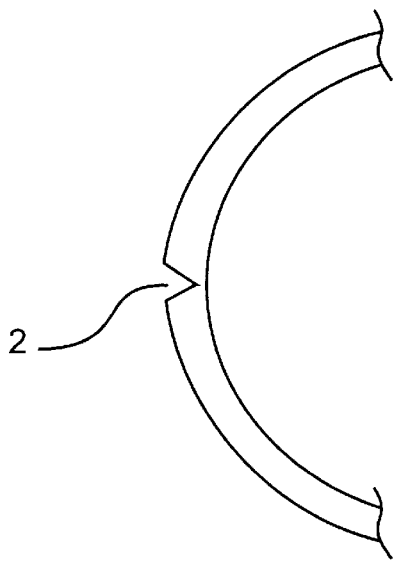
FIG. 2 depicts a close up view of Item 2, the notch.
Figure 3:
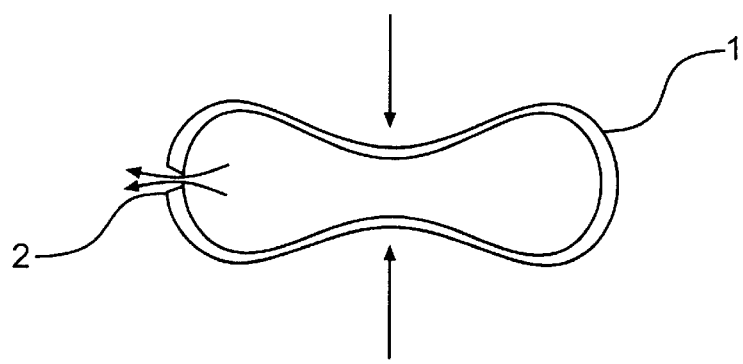
FIG. 3 shows pressure being applied to the sides of the capsule and the pre-cut surface rupturing, spraying the contents out in one squirt of the collapsing capsule.

Operation—FIGS. 1–3 Capsule with semi-perforated tip

Hold the capsule in one hand, point at the other hand and squeeze the capsule until the semi-perforated tip bursts and sprays the solution onto the other hand. Toss the capsule away and rub both hand coating with the sanitizing solution with dries in several seconds.

Operation—FIG. 4 Capsule with plug tip

One hand operation: This can be done in your pocket. Hold the capsule in one hand and with you finger nail pry off the tip plug. Squeeze the capsule dispensing the solution in the same hand. Toss away the capsule. The solution in now in one hand. At a convenient moment, bring both hands together and coat both hands. Solution air-dries in several seconds.

Operation—FIG. 5, 7–10, 13 Capsule, sphere/ball, disk, tube and flat pack with pre-cut slit and cover One hand operation: This can be done in your pocket or under a table. Hold the enclosure in one hand with the cover tab towards you thumb. Pry off the cover with your fingernail. Squeeze the enclosure until the substance dispenses into your hand. At a convenient moment, bring both hands together and coat both hands. Solution air-dries in several seconds.

Two-hand operation: This is done when you are able to use two hands or when the cover is a tape with tab. Hold the enclosure in one hand. With the other hand, grab the tab and pull off the cover. Bring both hands together and coat both hands. Solution air-dries in several seconds.

Operation—FIG. 6 Capsule with two halves

With both hands, pull the capsule apart. Squeeze the halves into the hands. Rub hands together. Solution air-dries in several seconds.

Operation—FIG. 11 Tube with clamped ends

With both hands, remove the clamp and squeeze the tube dispensing the solution into one hand. Rub hands together. Solution air-dries in several seconds.

Operation—FIG. 12 Tube with folded ends

One hand operation: With one hand, hold the tube and with the thumbnail pry open the folded end then turn the tube around and squeeze solution into the hand. Rub hands together. Solution air-dries in several seconds.

Operation—FIG. 14 Flat Pack with notched end

Hold packet in one hand. With the other hand, grasp the notched end and tear off the end. Squeeze the packet into one hand. Rub hands together. Solution air-dries in several seconds.

Operation—FIG. 15 Flat Pack with folded ends

Hold the packet in one hand. With the thumb, break the adhesive seal and unfold the end. Squeeze the container and dispense the solution into one hand. Rub hands together. Solution air-dries in several seconds.

Operation—FIG. 16 Flat Pack with jagged edges

Hold packet in one hand. With the other hand, grasp the jagged end and tear off a corner. Squeeze the packet into one hand. Rub hands together. Solution air-dries in several seconds.

Conclusion, Ramifications, and Scope

The reader can see that the micro hand sanitizer substantially differs from current approaches because it is single use with:

volumetric capacity less that 2 milliliters, simple, rapid dispensing methods.

These differences from conventional methods allow for micro packets to be carried in shirt pockets, pants pockets or confined areas where bottles won't fit. I allow the user to carry one "just in case" for defense against bacterial, viral, and biological agents.

The single use feature:

Allows for the simple designs because resealing is not required;

also avoids the requirement to watch and determine how much is being dispensed; and, allows for bulk quantities to be placed in areas of potential contamination e.g. public restrooms, food preparation areas, areas which handle money, or areas where contamination is suspected.

The micro hand sanitizer can be used in an inconspicuous way in a crowd of people. The one hand opening method discussed allow for opening in a pocket or under a desk that does not require one's full attention. The user can still focus on ongoing activities. Other methods washing hand, towels, or bottles are too restricting.

The micro hand sanitizer can be used in a limited sense to sanitize doorknobs, telephone hand-sets, pens, or other high use small items.

The ramifications of the micro hand sanitizer will be significant in today society where increasing personnel contact takes place in public places and the transmission of bacterial and viral germs are constantly increasing. The MHS solution is strong enough to be a deterrence constant threat of biological agents that are transmitted on surfaces. The more common use of MHS may significantly impact a percentage of societies' heal and provided limited protection from deliberate threats.

Thus the scope of the micro hand sanitizer invention should be determined by the appended claims and their legal equivalents, rather than by the examples given.

What I claim as my invention is:

1. A sanitizing system comprising:

an encapsulating container sized to be held and opened between two fingers and composed of a disposable material which is capable of only single use;

sanitizing substance contained within the miniature encapsulating container;

said encapsulating container holding about 0.25 to 5.0 milliliters of said sanitizing substance;

said encapsulating container has a shape selected from the group consisting of a sphere, cylinder, capsule and disk; and an encapsulated opening system located on one end or location on said encapsulating container selected from the group consisting of configurations using a semi-perforated hole, incision or a manufactured thin area, which allows quick and directional dispensing of the sanitizing substance once the container has been opened.

2. The sanitizing system of claim 1, where the container is comprised of a material selected such that sufficient squeezing force causes the container to burst open at a predetermined location.

3. The sanitizing system of claim 1, wherein said sanitizing solution has at least one active ingredient selected to defeat biological agents.

4. The sanitizing system of claim 1, wherein the said sanitizing solution has at least one active ingredient selected to counter chemical agents.

5. A method of using a sanitizing substance to sanitize a person's hands and other small areas, comprising the steps of obtaining a container containing a sanitizing substance and sized to be concealable with one hand of the person, holding the container by two fingers of the one hand or within the palm of the one hand, opening the container with the one hand or with at least one finger of the person's other hand, and dispensing substantially all of the sanitizing substance in the container to the person's one hand or the other hand or to a small area on another object to be sanitized.

* * * * *